United States Patent [19]

Daniel

[11] 4,021,522
[45] * May 3, 1977

[54] METHOD OF FORMING COLLAGEN DISPERSIONS

[75] Inventor: Leonard Daniel, Grays Point, Australia

[73] Assignee: Collagen Products Pty. Limited, Australia

[ * ] Notice: The portion of the term of this patent subsequent to July 8, 1992, has been disclaimed.

[22] Filed: June 26, 1975

[21] Appl. No.: 590,611

Related U.S. Application Data

[63] Continuation-in-part of Ser. No. 395,994, Sept. 10, 1973, Pat. No. 3,894,132.

[52] U.S. Cl. .............................. 264/138; 8/94.11; 128/335.5; 260/123.7; 264/152; 426/140
[51] Int. Cl.$^2$ ..................... A61L 17/00; C07G 7/00
[58] Field of Search ................ 8/94.11; 260/123.7; 264/138, 152, 202

[56] References Cited

UNITED STATES PATENTS 3,894,132  7/1975  Daniel ............................. 264/138

Primary Examiner—Donald E. Czaja
Assistant Examiner—H. H. Fletcher
Attorney, Agent, or Firm—Giles C. Clegg, Jr.

[57] ABSTRACT

A method of preparing collagen fibre dispersions comprising treating a collagenous material such as hide corium with a solution containing an alkaline earth metal hydroxide and an alkaline earth hydroxide; coarsely dicing or mincing the collagen, and mechanically dispersing the diced or minced collagen to achieve longitudinal separation of the collagen fibres; the dicing or mincing of the collagen being controlled such that at least 95% by weight of the collagen fibres in the dispersion are retained after neutralization on a 297 micron U.S. standard sieve.

19 Claims, No Drawings

METHOD OF FORMING COLLAGEN DISPERSIONS

This is a continuation in part of U.S. patent application Ser. No. 395,994 filed Sept. 10, 1973, U.S. Pat. No. 3,894,132.

The present invention relates to a method of forming a dispersion of collagen fibres and to dispersions so formed.

The white connective tissue of animals comprises a composite of collagen fibres which are exceptionally strong and have only short range elasticity, and interfibre materials which are gel-like in nature. Connective tissue exists in the animal body in a wet condition and has therefore evolved to show natural characteristics of wet strength. Naturally occuring connective tissue is used to form leather sausage skins and catgut however the irregular and variable shape of naturally occuring connective tissue is a serious disadvantage in the production of these products. Numerous workers in the art have sought a method of breaking down the naturally occuring connective tissue and reforming it into a new shape.

The most readily available form of connective tissue is animal skins. In these skins the collagen fibres constitute a dense three dimensional feltwork interconnected by interfibre material. Due to the extensive entanglement of the fibres with one another workers in the art have considered that the only way to break down the connective tissue is to sever it into microscopic particles as by colloid milling. The natural corollary of such a process is that a product reconstituted from the collagen dispersion so formed will have very limited inherent wet strength and tear resistance. The wet strength of the reconstituted product will be limited to the adhesion between individual microscopic particles of collagen; there will be no collagen fibres coursing through the product to give inherent wet strength and tear resistance as there are in the natural product.

U.S. Pat. No. 3,634,561 to Hawkins et al discloses a process for the preparation of a collagen dispersion in the form of a dough. The process involves colloid milling the collagenous starting material until the dispersion shows on extractability within a range of 8% to 16% on a dry weight basis, a solids content within the range of 4.5% to 6.5% dry weight basis and an apparent viscosity between 45 and 80 poises. The colloid milling required to give the defined extractability, typically nine (9) passes through a colloid mill, reduces the particles of collagen to a microscopic size with the result that articles manufactured from the dispersion have a very low inherent wet strength.

An object of the present invention is to produce dispersion of collagen fibres which still retain the fibrous character of the natural product and have not been milled down to a microscopic, ultra-short state. The dispersions according to this invention can be formed into articles which show an improved inherent wet strength and tear resistance compared with such articles when made from the prior art processes by virtue of the creation in the article of a tissue structure similar to that of the natural.

The present invention consists in a method of forming a dispersion of collagenous fibres, comprising the steps of:

a. treating a collagenous material with an aqueous solution of alkaline earth metal hydroxide and an alkali metal hydroxide to reduce cohesion between the collagen fibres present in the material, the alkali metal hydroxide having a concentrate of from 0.25 to 2 molar and the treatment being carried out at a temperature between the freezing point of the mixture and 30° C;

b. severing the collagenous material into particles; and c. mechanically dispersing the collagen fibres to free the fibres from one another substantially along their whole length and substantially without further reduction of the fibre length, the size of the particles of step (b) being such that at least 95% by weight of the fibres obtained in step (c) are retained after neutralisation on a 297 micron U.S. standard sieve when a sample of the fibres is placed on the screen and flushed with water.

It has been found by the present inventor that if at least 95% of the fibres in the dispersion are retained after neutralisation on a 297 micron U.S. standard screen when a sample of the fibres is placed on the screen and flushed with water then products produced from the dispersion will show improved inherent wet strength and tear resistance compared with products produced by the prior art proposals.

The fibrous dispersion produced by the present method are quite distinct from that produced by the prior art as exemplified by U.S. Pat. No. 3,634,561. When a dispersion according to Example 1 of U.S. Pat. No. 3,634,561 was prepared it was found that at least 95% by weight of the collagen was flushed through the 297 micron U.S. standard sieve. The difference is further highlighted by the requirement of the prior art patent that the dispersed collagen must show an extractability of from 8% to 16%. To be extractable the collagen must be in the form of single tropo-collagen molecules i.e. ultramicroscopic particles having a length of about 3000 Angstroms. The process according to the present invention is specifically intended to minimise the production of these ultrafine particles. When dispersions according to the present invention were tested for their extractability by the process described in U.S. Pat. No. 3,634,561 the extractability was so low as to be unmeasurable i.e. less than 0.1% by weight.

The specific alkali metal hydroxide and alkaline earth metal hydroxide pretreatment according to this invention, combined with the severing step enables the fibres to be separated from one another without further length shortening under a suitable applied mechanical force. The applicant is therefore able for the first time to produce a collagen dispersion which can be reformed into articles which will have an inherent wet strength and tear resistance.

The alkali metal hydroxide treatment should be continued for a period sufficient to ensure the breakdown of the interfibrilar cement without being prolonged to an extent likely to lead to breakdown of the fibres themselves, a long period of treatment is acceptable if excess treatment solution is removed after initial softening and the material stored under cool, moist conditions.

Simple experimentation will reveal to the skilled worker the best treatment time for any particular combination of collagenous material, alkali metal hydroxide and temperature. The examples set out hereafter describe in detail the determination of the most suitable time for the alkali metal hydroxide treatment under a given set of conditions.

The most preferred alkali metal hydroxides are lithium, sodium and potassium hydroxides. It is preferred that the hydroxide is present in an amount of from 0.4 to 0.9 molar.

The alkaline earth metal hydroxide has a further advantageous effect in that it substantially reduces the slipperyness of the collagenous material after it has been treated with the alkaline metal hydroxide. While a certain slipperyness of the fibre surface is desirable in that it facilitates the longitudinal separation of the fibres during mashing the presence of the alkali earth metal ions tempers this character and facilitates maintenance of the material to be mashed between the mashing surfaces of the mashing machine. A balance may thus be achieved between the desirable separation of the fibre and the ease of transmission of shear forces to the fibres to effect the separation.

The pre-treatment with the alkaline earth hydroxide has also been found to assist in the prevention of any tendancy for the individual fibres to break up under the mashing beyond that earlier obtained by mincing or dicing. Any breaking up of the individual fibres would produce an undesirable variation in fibre length; in carrying out the present invention conditions under which fibre break up occurs are to be avoided.

The severing of the collagenous material into discrete particles may advantageously be achieved either by mincing or by dicing the collagenous material. The size of the discrete lumps formed by the severing step will determine the staple length of the fibres in the dispersion produced in the mashing step. It is thus very desirable to ensure that the dicing or mincing is carried out as evenly as possible to ensure a uniform staple length of the fibres in the resulting dispersion.

If desired the step of treating the collagenous material with an alkali metal hydroxide and/or the step of severing the collagenous material into discrete particles may preceed the final mashing step by a period of time which may be up to as long as several months. This storage of the partly treated collagen may be used to impart special characteristics to the fibres in the resulting dispersion.

The severing step is conveniently carried out by mincing the collagenous material using a mincer having ⅜ inch diameter holes, the lumps of collagenous material resulting from this mincing step will have a major diameter of from about 3 to about 10mm. The fibres resulting from the mechanical dispersion of such lumps show a relatively uniform fibre length and are sufficiently long to ensure a high inherent wet strength and tear resistance in articles formed from the fibres.

The selection of the minimun size of the severed lumps of collagenous material will depend to some degree upon the statistical size distribution of the size of the lumps, and of the individual fibres within the lumps; this will vary with the exact severing method used. For any given system simple routine testing of samples will reveal when the severing is getting down to a degree where about 5% by weight of the neutralised fibres will pass through a 297 micron U.S. standard screen (A.S.T.M. E-11-61) when gently flushed with water. It should be noted that if the fibres in an alkaline condition were flushed with water uncontrolled swelling of the collagenous fibres would take place. If the collagenous fibres are neutralised before testing significant swelling will not take place. The neutralisation should take place without the addition of excess water, various advantageous methods for the neutralisation of the collagenous fibres are discussed later in this specification. If the severing step has been carried too far the material should be rejected. If none of the fibres pass through the filter it is acceptable provided that the fibres have been adequately separated from one another along their entire length i.e. that the collagen fibres have been "disentangled" from one another.

The mechanical dispersion of the collagen fibres is preferably carried out with a mashing action which includes a downward bruising stroke and a lateral smearing stroke to promote longitudinal separation of the fibres. A clear distinction must be made between this mashing or smearing step which achieves longitudinal separation of fibres while maintaining their length and conventional mincing processes using a mincer or colloid mill which results in transverse cutting of the fibres with a resultant diminution in fibre length.

In a further embodiment of the invention dispersion of the collagen fibres is achieved by extruding the collagenous material through a narrow slit. The width of the slot will determine the fibre size in the dispersion and simple experimentation will determine the best slot width. A slot width of 0.1 mm has been found suitable for the dispersion of cowhide which has been treated with calcium and sodium hydroxides. Prepassage through a slot of 0.3 mm assists in achieving complete dispersion, additionally the collagenous material may be minced or diced prior to its extrusion through the slots.

It is highly desirable that the collagenous material is initially subjected to a pretreatment with an aqueous solution of an alkaline earth metal hydroxide, preferably calcium hydroxide or strontium hydroxide or mixtures thereof, until the collagenous material is penetrated by, and preferably saturated with the alkaline earth metal hydroxide. It has been found that this pretreatment serves to restrain and control the swelling of the fibres such that the network cohesion of the collagenous material may be more readily eliminated without parallel destruction of individual fibre integrity.

It is preferred that after mechanical dispersion of the fibres the dispersion is treated to remove excess alkali. The removal of the alkali should be effected in such a manner that further swelling of the fibres is avoided; this in essence means that water availability must be severly limited. A number of ways are available for achieving removal of the excess alkali. However, one or other of the following processes is preferred.

a. The dispersion may be washed with saturated sodium sulphate.

b. Pulverised solid acids, such as adipic, citric, or tartaric acids, or the addition of acid salts such as sodium dihydrogen phosphate or sodium dihydrogen citrate, or buffer mixtures may be added to the fibre dispersion while mixing the dispersion, as in a dough mixer. If desired small quantities of water may be added to the mix to adjust the texture of the dispersion.

c. liquid acids such as hydrochloric acid, acetic acid, or lactic acid in concentrated form may be applied to the dispersion as a mist spray.

d. Carbon dioxide under pressure may also be used. This procedure is particularly appropriate to the requirements of the applicant's copending patent application entitled "A method for the formation of articles from collagenous material" Ser. No. 395,943 filed Sept. 10, 1973.

e. The alkali metal hydroxide may be leached from the dispersion by solvent leaching using aliphatic alcohols. A mixture of four parts by volume of rectified spirit and one part by volume of water has been found to neither increase or decrease the water content of the fibres while effectively leaching the alkali from the dispersion.

With respect to the mashing and neutralisation of the dispersion two great advantages accrue from the use of this invention in conjunction with the applicant's copending patent application referred to above. Firstly the dispersion does not have to be completely neutralised, nor does it have to be rendered acid. Secondly any residual incomplete fibre separation at the mashing stage or moderate re-entanglement at neutralisation can be accomodated at a later stage due to the lubricating action of the propylene glycol alginate added to the dispersion in the course of the process described in the said patent application Ser. No. 395,943. The separation of the fibres may be increased by subsequently re-extruding the mixture through a slot of the dimensions referred to above. It will be appreciated that in order to avoid weak spots in the final product, a facility for complete fibre separation and smooth relative motion at reshaping must be available.

Following neutralisation, or substantial neutralisation, conventional, fibre handling techniques may be used with the proviso that elevated temperatures should be avoided if preshrinking of the fibres is to be avoided. The dispersion may conveniently be washed in an appreciable volume of water and drained on a relatively coarse screen, i.e. having holes of a diameter of the order of 1 mm., under an applied squeezing pressure. The fibres may be washed sufficiently to remove soluble salts and fine particulate matter, such as insoluble calcium salts, to produce clean approximately neutral collagen fibres of essentially uniform staple length.

The washed preparation formed by this process may be applied directly to, or may be heat contracted for, the process of the applicant's copending patent application. Alternatively excess water may be removed by solvents or by fat-liquoring followed by air drying. If solvent drying is used the most preferred solvents are acetone, methyl ethyl ketone and ethanol. The solvent drying is also preferably followed by air evaporation to leave white, pure, stable, collagen staple fibres which are readily rewettable. The air dried preparations are stable. However, it is necessary to store water-wet fibres under refrigeration.

The process according to this invention may be applied to any connective tissue i.e. collagen containing raw material, irrespective of whether it has been dried out for storage and shipment or whether it has been maintained in the wet state. Skin corium is preferred because of its content of long strong fibres; tendon is normally in short supply and presents no particular advantages; ossein i.e. the connective tissue of bone, does not yield long fibres and if this material is used it would be necessary to use a washing retention screen finer than that described above.

Hereinafter described by way of example only are examples of the process according to the present invention.

EXAMPLE 1

Salted hide was washed free from salt, limed with an excess of unsharpened lime for 4 days, unhaired and fleshed. Aliquots of the corium were immersed in a definite but not large excess (to allow for fluid uptake by the tissue) of 3% and of 2% solutions of sodium hydroxide, and left at ambient room temperature (daytime temperature around 26° C). In two days the 3% level was found to be a little over-softened, the 2% level required 5 days for treatment. In each case the softened material was drained the grain removed for separate examination, and the corium split put through a mincing machine using a coarse plate, (⅜ inch diameter holes). The mince was carefully mashed with an impact/smearing action to free and separate the fibres, the grain membrane being similarly treated separately. The mash was placed into a dough-mixer and whilst mixing, sufficient pulverised solid sodium dihydrogen phosphate to achieve neutralisation was dusted in so as to progressively dissolve. After neutralisation the mix was diluted with cold water and the wash-extract removed by squeezing the pulp in nylon stocking; all of the fibre was retained by the pressure expanded mesh, thus demonstrating the absence of finely broken up fibre material. The dilution/wash process was repeated once more to yield clean, white, essentially neutral, discrete collagen fibres of essentially uniform length which was substantially all retained on a 297 micron U.S. standard screen. The grain material produced was satisfactory but predominantly of shorter fibre length. All samples yielded good tissues when processed according to the applicant's copending patent application Ser. No. 395,943; however, for good quality films from grain membrane it is essential that all of the hair shall have been removed, otherwise the stubs will appear as foreign inclusions.

EXAMPLE II

Matched samples of dried limed splits (an article of commerce) were immersed in an excess of each of 1%, 2, 4, 6, 8, 10, 20 and 30 percent sodium hydroxide at day air temperatures around 20, 22° C. The results together with those of the previous example will indicate the general pattern of alkali concentration response. After one day in the 30% solution the splits had lost a lot of surface material into solution, but the centre material remaining was very hard; i.e. there was maximal (surface) erosion of the material with no penetration beyond the erosion interface. The 20% sample was similar but less extremely affected.

Still after one day, the 10% level material was reasonably well swollen (i.e. due to some penetration) and was jellied at the edges together with fine material dispersed in the solution, but with still hard substance at the centre of the splits. The 8% level: swollen, slushy on the outside with some breakup, some pieces soft in the centre but others in about equal proportion still firm there. Thus solution penetration and material swelling was replacing material erosion and dispersal as the alkali concentration was reduced.

At the 6% level, the splits were swollen, the cut edges were fragmenting but going to jelly on the exterior of one specimen only. 4%: swollen with the cut edges showing some fragmentation; firm in the centre but tending to soft on the outside. 2%: not much swollen, but still uniformly firm. 1%: little swollen; hard; i.e. at this level, no swelling and no erosion.

The splits treated at the 2% level were found to be sufficiently softened after 5 days, those at the 1% level not even after 10 days.

For further processing the splits softened with 2% sodium hydroxide for 5 days were drained, minced and mashed as in Example 1. The excess alkali was removed by macerating the pulp with two successive aliquots of a mixture of four parts of rectified spirit together with one part of water followed by pressing out of the fluid. For a third maceration the spirit : water mix was acidulated with acetic acid. Finally the fibrous pulp was dispersed in water for washing essentially as in example 1.

EXAMPLE III

Sodium hydroxide has a molecular weight of 40, that of lithium hydroxide monohydrate is 42, i.e. the difference is negligible for practical purposes. Limed hide and dried limed splits were exposed to 1%, 2% and 3% solutions of lithium hydroxide monohydrate in the manner previously applied using sodium hydroxide. Daytime temperatures were around 20° C. As with sodium hydroxide, adequate softening was achieved at the 3% level, essentially in two days, whereas the 2% level required five days, at which time the 1% level was still much too firm.

The molecular weight of potassium hydroxide is 56, hence in order to achieve molecular concentration equivalent to sodium hydroxide with this alkali the sodium hydroxide figures have to be multiplied by 1.4. Of course in actual practice all concentrations are determined by analysis, and since for example potassium hydroxide pellets are never 100% further weight adjustments are made on the analysis basis. Dried limed splits were immersed in potassium hydroxide solutions of equivalent alkali concentration to that of 1% 2% and 3% sodium hydroxide. On this occasion the daytime air temperature was around 26° C. The following pattern of response was observed:

| Interval | Alkali Concentration Level | | |
|---|---|---|---|
| | Lower | Middle | Top |
| 1 day | not swollen firm | swollen, little softening | swollen, some softening |
| 2 days | now swelling some softening | softened | oversoft |
| 3 days | softening | oversoftened | breaking up |
| 4 days | still insufficiently softened | — | — |

The accelerating effect of the higher temperature will be apparent.

EXAMPLE IV

Salted hide was washed free from excess salt and immersed in water carrying an excess of strontium hydroxide. After four days the hide was removed, unhaired and fleshed. The corium had swelled more than is normal with the use of calcium hydroxide (lime). Next the corium was cut up into suitably matched pieces one set of which was retained in strontium hydroxide as controls; the others were dispersed into aliquots of 1%, 2% and 3% sodium hydroxide of sufficient volume to cover the material well but not excessively. Daytime temperatures were around 22° C. After one day's exposure, hide swelling had increased in line with sodium hydroxide concentration, none were sufficiently softened. From then on the softening pattern was as follows:-

| Interval | Control | 1% level | 2% level | 3% level |
|---|---|---|---|---|
| 2 days | firm | some softening | noticeably softened | good condition |
| 3 days | firm | softness increasing | fairly soft | thoroughly softened; no material breakup |

EXAMPLE V

Ossein was prepared from the shaft bones of sheep legs and each shaft cut along its length to allow removal of the fatty integument to the marrow canal. The corresponding leg tendons were cut away and their enclosing sheaths removed. Matched samples of ossein, and of tendon were prepared, half of which were limed for 4 days, the remaining half being stored under distilled water in the body of a refrigerator. Surface lime was removed from the limed samples and the matched sets of limed vs unlimed, ossein and tendon distributed into aliquots of 1%, 2% and 3% sodium hydroxide. Daytime air temperatures were around 25° C. The results are given in the table.

EXAMPLE V - TABLE

| Exposure Interval | Material | SODIUM HYDROXIDE CONCENTRATION | | | | | |
|---|---|---|---|---|---|---|---|
| | | 1% | | 2% | | 3% | |
| | | Unlimed | Limed | Unlimed | Limed | Unlimed | Limed |
| 1 day : | Ossein | hard | hard | hard | a little swelling and softening. | Swollen, somewhat softened slippery. | swollen, softened. |
| 2 days: | | hard. | a little swollen | firm | softening | softened, swollen and breaking up in liquor | soft; well swollen but not breaking up in liquor. |
| 3 days: | | hard | hard | softening | softened | — | — |
| 1 day : | Tendon | soft, transparent slippery | soft, good condition | softened but extremely slippery | softened conditioned a bit slimy | very swollen sloppy | satisfactory condition; a little slippery |
| 2 days: | | partly softened fibres not easily separable | mashable, fibres separable | mashable; fibres swollen | easily mashable; fibres defined | very soft, easily dispersed fragmenting in liquor | slightly oversoft samples discrete in liquor. |

The claims defining the invention are as follows:
1. A method of forming a dispersion of collagenous fibres comprising the steps of:
 a. treating a collagenous material with an aqueous solution of an alkaline earth metal hydroxide and an alkali metal hydroxide to reduce the cohesion between the collagen fibres, present in the material, the alkali metal hydroxide having a concentration of from 0.25 to 2 molar and the treatment being carried out at a temperature between the freezing point of the mixture and 30° C;

b. severing the collagenous material into particles; and c. mechanically dispersing the collagen fibres to free the fibres from one another substantially along their whole length and substantially without further reduction of the fibre length, the size of the particles of step (b) being such that at least 95% by weight of the fibres obtained in step (c) are retained after neutralisation on a 297 micron U.S. standard sieve when a sample of the fibres is placed on the screen and flushed with water.

2. A method as claimed in claim 1 in which the mechanical dispersion of the collagen fibres is achieved by mashing.

3. A method as claimed in claim 1 in which the mechanical dispersion of the collagen is achieved by extrusion through a restricted aperture.

4. A method as claimed in claim 1 in which the alkali metal hydroxide is chosen from the group comprising lithium hydroxide, sodium hydroxide and potassium hydroxide.

5. A method as claimed in claim 1 in which the alkali metal hydroxide is present in a concentration of 0.4 to 0.9 molar.

6. A method as claimed in claim 1 in which the collagenous material is severed into discrete particles by mincing or dicing.

7. A method as claimed in claim 1 in which the alkaline earth metal hydroxide is selected from the group consisting of calcium hydroxide and strontium hydroxide.

8. A method as claimed in claim 1 in which the collagenous dispersion is at least substantially neutralized after being mechanically dispersed.

9. A method as claimed in claim 8 in which the neutralisation is effected by a method selected from the group consisting of:-
a. washing with a saturated solution of sodium sulphate.
b. addition of a pulverised solid acid, acid salt or buffer mixture.
c. application of a mist spray of a concentrated liquid acid,
d. application of carbon under pressure
e. solvent leaching 10. A method as claimed in claim 9 in which the collagenous dispersion is dried after being neutralised.

11. A method as claimed in claim 10 in which the dispersion is dried by washing in a solvent selected from the group consisting of acetone, methyl ethyl ketone and alcohol, and air drying.

12. A method as claimed in claim 10 in which the dispersion is dried by fat liquoring followed by air drying.

13. A method as claimed in claim 1 which the collagenous material is skin corium.

14. A method of forming a dispersion of collagenous fibers comprising the steps of:
a. treating a collagenous material with an aqueous solution of an alkaline earth metal hydroxide and an alkali metal hydroxide to reduce the cohesion between the collagen fibers, present in the material, the alkali metal hydroxide having a concentration of from 0.25 to 2 molar and the treatment being carried out at a temperature between the freezing point of the mixture and 30° C;
b. severing the collagenous material into particles; and
c. mechanically dispersing the collagen fibers to free the fibers from one another substantially along their whole length and substantially without further reduction of the fiber length, the size of the particles of steb (b) being such that the fibers obtained in step (c) are substantially retained on a screen having holes in the order of 1 m.m. in diameter if after neutralization and washing they are drained on said screen.

15. A method as claimed in claim 14 in which the mechanical dispersion of the collagen fibers is achieved by mashing.

16. A method as claimed in claim 14 in which the mechanical dispersion of the collagen is achieved by extrusion through a restricted aperture.

17. A method as claimed in claim 14 in which the alkali metal hydroxide is chosen from the group comprising lithium hydroxide, sodium hydroxide and potassium hydroxide.

18. A method as claimed in claim 14 in which the alkali metal hydroxide is present in a concentration of 0.4 to 0.9 molar.

19. A dispersion of collagen fibers formed by the method of claim 15.

* * * * *